United States Patent [19]

Schönafinger et al.

[11] Patent Number: 5,221,680

[45] Date of Patent: Jun. 22, 1993

[54] SUBSTITUTED 3-AMINOSYDNONIMINES

[75] Inventors: Karl Schönafinger, Alzenau; Rudi Beyerle, Frankfurt; Helmut Bohn, Schöneck, all of Fed. Rep. of Germany

[73] Assignee: Cassella Aktiengesellschaft, Frankfurt am Main, Fed. Rep. of Germany

[21] Appl. No.: 842,435

[22] Filed: Feb. 27, 1992

Related U.S. Application Data

[63] Continuation of Ser. No. 598,037, Oct. 16, 1990, abandoned, which is a continuation of Ser. No. 290,615, Dec. 27, 1988, abandoned.

Foreign Application Priority Data

Jan. 14, 1988 [DE] Fed. Rep. of Germany ....... 3800830

[51] Int. Cl.$^5$ .................. A61K 31/435; C07D 413/04
[52] U.S. Cl. ..................... 514/326; 514/318; 544/582; 544/60; 544/138; 544/367; 546/193; 546/209; 548/125
[58] Field of Search ............... 546/193, 209; 514/326, 514/318

[56] References Cited

U.S. PATENT DOCUMENTS

| | | | |
|---|---|---|---|
| 3,312,690 | 4/1967 | Masuda et al. | 260/239 |
| 3,769,283 | 10/1973 | Masuda et al. | 260/247.2 |
| 4,305,939 | 12/1981 | Schöafinger | 424/246 |
| 4,937,244 | 6/1990 | Schönafinger | 514/252 |

FOREIGN PATENT DOCUMENTS

| | | |
|---|---|---|
| 0059356 | 5/1985 | European Pat. Off. . |
| 0276710 | 8/1988 | European Pat. Off. . |
| 1620501 | 4/1970 | Fed. Rep. of Germany . |
| 2271818 | 12/1975 | France . |

*Primary Examiner*—Donald G. Daus
*Assistant Examiner*—Philip Datlow
*Attorney, Agent, or Firm*—Perman & Green

[57] ABSTRACT

Substituted 3-aminosydnonimines of the formula I

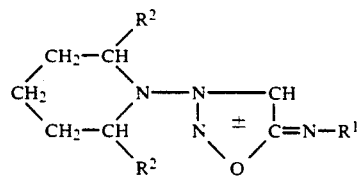

and pharmacologically acceptable acid addition salts thereof, in which $R^1$ denotes hydrogen or the radical —$COR^4$, $R^2$ denotes alkyl or phenyl alkyl having 1 to 4 C atoms in the alkyl group, $R^4$ denotes, for example, an aryl radical, and processes and formulations for controlling or preventing cardiovascular diseases by administering an effective amount of such compounds to a host in need thereof.

11 Claims, No Drawings

SUBSTITUTED 3-AMINOSYDNONIMINES

This is a continuation of application Ser. No. 07/598,037 filed on Oct. 16, 1990, now abandoned, which is a continuation of Ser. No. 07/290,615 filed Dec. 27, 1988, now abandoned.

The invention relates to pharmacologically active substituted 3-aminosydnonimines of the general formula I

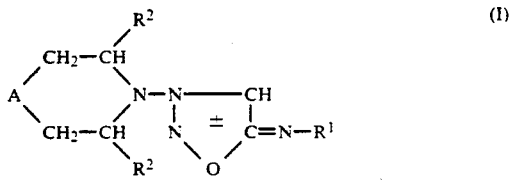

and to the pharmacologically acceptable acid addition salts thereof, in which

A denotes the radical —$CH_2$—, —O—, —$S(O_n)$—, —$N(R^3)$— or a direct bond, $R^1$ denotes hydrogen, nitroso (—NO) or the radical —$COR^4$, $R^2$ and $R^3$ denote alkyl having 1 to 4 C atoms or phenylalkyl having 1 to 4 C atoms in the alkyl radical, $R^4$ denotes an aliphatic radical which has 1 to 6 C atoms and can also be substituted by alkoxy having 1 to 6 C atoms or by an aliphatic thio radical having up to 4 C atoms; a cycloaliphatic radical having 5 to 7 C atoms; a bicycloaliphatic radical having 7 to 14 C atoms; a tricycloaliphatic radical having 7 to 16 C atoms; an alkoxy radical which has 1 to 18 C atoms and can also be substituted by alkoxy having 1 to 6 C atoms; an aryloxy radical having 6 to 10 C atoms; an alkoxycarbonyl radical having a total of 2 to 7 C atoms; an aryl radical having 6 to 10 C atoms; an aryl radical which has 6 to 10 C atoms and is mono-, di- or trisubstituted by 1 to 3 halogen atoms and/or 1 to 3 alkyl radicals having 1 to 4 C atoms and/or 1 to 3 alkoxy radicals having 1 to 4 C atoms and/or 1 or 2 nitro groups and/or 1 or 2 hydroxyl groups and/or 1 or 2 nitro groups and/or 1 or 2 hydroxyl groups and/or 1 or 2 alkylcarbonyloxy radicals having 1 to 4 C atoms, and/or 1 to 3 alkylthio radicals having 1 to 4 C atoms and/or a trifluoromethyl radical and/or an imidazole radical; imidazolyl; pyridyl; thienyl; styryle; n denotes the number 0, 1 or 2.

The invention furthermore relates to a process for the preparation of the compounds I according to the invention and to the use thereof.

If A denotes one of the radicals —$CH_2$—, —O—, —$S(O_n)$— or —$N(R^3)$— there is in the 3-position of the sydnonimine the radical of a heterocyclic 6-membered ring which has one hetero atom (N) or which has two hetero atoms (N, O or N,S or N,N) and which is substituted in the stated manner. If A denotes a direct bond there is in the 3-position of the sydnonimine a pyrrolidine radical which is disubstituted in the 2,5-positions.

Aliphatic radicals, thio radicals, alkyl radicals and alkoxy radicals can be straight-chain or branched. This also applies when they occur as substituents of other radicals, for example as substituents of aryl radicals, or in conjunction with other radicals, for example as phenalkyl, as alkoxycarbonyl, as alkylcarbonyloxy or as alkoxyalkoxy.

Preferred for A are the direct bond and the bivalent radicals: —$CH_2$—, —O—, and —$S(O_2)$—, of which the radical —$CH_2$— is particularly preferred.

The alkyl or phenalkyl radicals representing $R^2$ and $R^3$ can be identical or different. The radicals $R^2$ are preferably in cis-position relative to one another.

Examples of suitable phenalkyl radicals representing $R^2$ and/or $R^3$ are benzyl, 2-phenethyl, 3-phenylpropyl and 3-phenyl-butyl. Examples of suitable alkyl radicals representing $R^2$ and/or $R^3$ are methyl, ethyl, n-propyl, i-propyl, n-butyl, i-butyl and tert.-butyl. Methyl is preferred for $R^2$ and/or $R^3$.

Particularly suitable aliphatic radicals representing $R^4$ are alkyl radicals, preferably having 1 to 4 C atoms. The aliphatic radicals, especially alkyl radicals, representing $R^4$ can also be substituted by alkoxy having 1 to 6 C atoms, in particular 1 to 4 C atoms, preferably 1 to 3 C atoms. Examples of alkyl and alkoxyalkyl radicals which can represent $R^4$ are: methyl; ethyl; n-propyl; i-propyl, n-, i-, sec.- and tert.-butyl; n- and i-pentyl; n- and i-hexyl; methoxy-, ethoxy-, n-propoxy-, i-propoxy-, n-butoxy-, i-butoxy-methyl; 2-methoxy-, 2-ethoxy-, 2-n-propoxy-, 2-i-propoxy-, 2-n-butoxy-ethyl; 2-methoxy-, 3-ethoxy-, 3-n-propoxy-, 3-i-propoxy-propyl or -i-propyl. The aliphatic radicals, especially the alkyl radicals, representing $R^4$ can also be substituted by an aliphatically substituted thio radical having up to 4 C atoms. Examples of such aliphatic thio radicals are alkylthio radicals having 1 to 4 C atoms, such as, for example, methyl-, ethyl-, n-propyl-, i-propyl-, n-butyl- and tert.-butyl-thio, but preferably allylthio ($CH_2$=CH—$CH_2$—S—). Particularly suitable cycloalphatic radicals representing $R^4$ are cycloalkyl radicals having 5 to 7 C atoms, in particular cyclopentyl, and preferably cyclohexyl. An especially suitable bicycloaliphatic radical representing $R^4$ is 2,6,6-trimethylbicyclo[3.1.1]heptan-3-yl (=3-pinanyl). An especially suitable tricycloaliphatic radical representing $R^4$ is tricyclo[3.3.1.1$^{3,7}$]decan-1-yl (=1-adamantyl).

The alkoxy substituents for the alkoxy radicals have, in particular, 1 to 4 C atoms. Examples of alkoxy radicals and alkoxyalkoxy radicals which can represent $R^4$ are: methoxy; ethoxy; n- and i-propoxy; n-, i-, sec.- and tert.-butoxy; n-pentyloxy; i-hexyloxy; n-octyloxy; n-docecyloxy; n-hexadecyloxy; n-heptadecyloxy; n-octadecyloxy; methoxy-, ethoxy-, n-propoxy-, i-propoxy-, n-butoxy-methoxy; 2-methoxy-, 2-ethoxy-, 2-n-propoxy-, 2-i-propoxy-ethoxy; 3-methoxy-, 3-ethoxy-, 3-n-propoxy-, 3-i-propoxy-propoxy; 4-methoxy-, 4-ethoxy-, 4-n-propoxy-, 3-propoxy-, 4-n-butoxy-butoxy.

The alkoxycarbonyl radical representing $R^4$ preferably has 2 to 5 C atoms. Examples which may be mentioned for this are: methoxy-, ethoxy-, n-propoxy-, i-propoxy-, n-butoxy- and i-butoxy-carbonyl. The ethoxycarbonyl radical is particularly suitable as alkoxycarbonyl radical representing $R^4$.

Examples of substituted and unsubstituted aryl radicals to be mentioned as representing $R^4$ are α- or β-naphthyl radicals, but especially the phenyl radical. Examples of aryloxy radicals to be mentioned as representing $R^4$ are α- or β-naphthoxy radicals, but especially the phenoxy radical. The aryl radicals representing $R^4$ can be mono-, di- or trisubstituted, but even with trisubstitution only a maximum of 2 nitro groups can be present, such as, for example, 2-methyl-4,6-dinitrophenyl and 2-chloro-6-methyl-4-nitrophenyl. In the case of voluminous substituents only a disubstitution or monosubstitution of nitro groups may be possible. Examples of suitable halogen substituents for the aryl radicals are fluorine, chlorine and/or bromine atoms. Examples of alkylcarbonyloxy substituents to be mentioned for the aryl radicals, especially for a phenyl radical, are: acetoxy, propionyloxy, n-butyryloxy and i-butyryloxy.

Examples of optionally substituted aryl radicals representing $R^4$ are: phenyl, 2-, 3- or 4-methyl-, -ethyl-, -n-propyl-, -i-propyl-phenyl; 2-, 3- or 4-methoxy-, -ethoxy-, -n-propoxy-, -i-propoxyphenyl; 2-, 3- or 4-fluoro-, -chloro- or -bromo-phenyl; 2-, 3- or 4-nitrophenyl; 2-, 3-or 4-hydroxyphenyl; 2-, 3- or 4-acetoxy-, -propionyloxy-, -n-butyryloxy-phenyl; 2,3-, 2,4-, 2,5- or 2,6-dimethyl-, -diethyl-, -dipropyl-phenyl; 2- or 3-methyl-4-chlorophenyl; 2-or 3-ethyl-4-fluorophenyl; 2-chloro-4-ethylphenyl; 2-bromo-4-i-propylphenyl; 2,6-diethoxy-4-chlorophenyl; 2,3,4-, 3,4,5- or 2,3,5-trimethyl-, -triethyl-, -tripropyl-, -trimethoxy-, -triethoxy- or -tripropoxy-phenyl; 2-hydroxy-3-, -4- or -5-chlorophenyl; 2-methyl-3-, -4- or -4-acetoxyphenyl.

Substituted aryl radicals to be particularly mentioned as representing $R^4$ are: methylphenyl (=tolyl), methoxyphenyl and chlorophenyl. The imdazolyl radical representing $R^4$ is preferably a 1-imidazolyl radical.

The following are preferred for $R^4$: methyl, ethyl, cyclohexyl, phenyl, 4-chlorophenyl, 4-methoxyphenyl, methoxy, ethoxy, n-propoxy, i-propoxy, n-decyloxy, n-octadecyloxy, 2-n-propoxy-ethoxy, 2-i-propoxy-ethoxy, n-butoxymethyl, 2-n-butoxy-ethoxy and allylthiomethyl.

n is preferably the number 2.

Preferred compounds of the formula I are those in which A denotes a direct bond, —$CH_2$— or —$S(O_2)$—, $R^2$ denotes methyl, and $R^1$ denotes hydrogen, —NO or —$COR^4$ with $R^4$=methyl, ethyl, methoxy, ethoxy, n- and i-propoxy, phenyl, cyclohexyl, allylthiomethyl, n-butoxymethyl or 2-n-butoxy-ethoxy.

A compound of the general formula I can be prepared in such a way that a compound of the general formula II

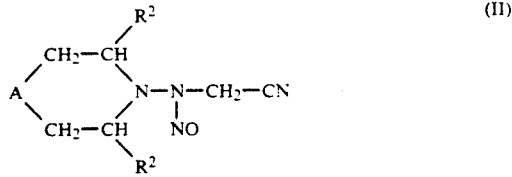

(II)

in which A and $R^2$ having the meanings already mentioned, is cyclized to give a compound of the general formula Ia

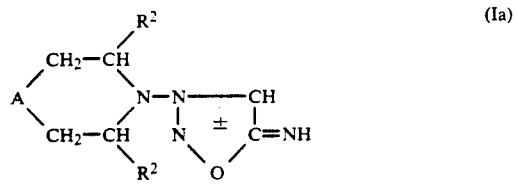

(Ia)

and that the latter, or an acid addition salt thereof, is, for the case where a compound of the formula I with $R^1$=—$COR^4$ is to be prepared, acylated with an acylating agent which introduces the radical —$COR^4$, or is, for the case where a compound of the formula I with $R^1$=—NO is to be prepared, nitrosated, and the resulting compound is, where appropriate, converted into a pharmacologically acceptable acid addition salt.

The cyclization of the compound II to give the compound Ia is carried out in a suitable organic or inorganic solvent, dispersant or diluent with the addition of a cyclizing agent, normally at temperatures from −10° to 40° C., in particular 0° to 40° C., preferably at 0° to 20° C.

Suitable cyclizing agents are those which set up a pH of 3or below in aqueous solution, that is to say, for example, strong acids such as mineral acids, such as sulphuric, nitric or phosphoric acid, preferably hydrogen chloride, or else strong organic acids such as sulphonic acids or trifluoroacetic acid. The cyclization is normally carried out while cooling in ice. 0.1 to 10 mol, preferably 1 to 5 mol, of the cyclizing agent is used, for example, based on 1 mol of the compound of the formula II. The cyclizing agent is normally used in excess. It is particularly convenient to use hydrogen chloride as cyclizing agent, which is normally passed into the reaction mixture to saturation. Normally obtained in the cyclization is the corresponding acid addition salt of the compound Ia.

Examples of suitable solvents, dispersants or diluents are: alcohols, for example those having 1 to 8 C atoms, especially those having 1 to 6 C atoms, preferably those having 1 to 4 C atoms, such as, for example, methanol, ethanol, i- and n-propanol, i-, sec- and tert-butanol, n-, i-, sec-, tert-pentanol, n-hexanol, 2-ethylbutanol, 2-ethylhexanol, isooctyl alcohol, cyclopentanol, cyclohexanol, methylcyclohexanol (mixture), benzyl alcohol; ethers, especially those having 2 to 8 C atoms in the molecule, such as, for example, diethyl ether, methyl ethyl ether, di-n-propyl ether, di-isopropyl ether, methyl n-butyl ether, methyl tert-butyl ether, ethyl propyl ether, di-butyl ether, tetrahydrofuran, 1,4-dioxane, 1,2-dimethoxyethane, bis-β-methoxyethyl ether; oligoethylene glycol dimethyl ethers such as, for example, tetraglyme or pentaglyme; alkyl carboxylates, especially those having 2 to 10 C atoms in the molecule, such as, for example, methyl, ethyl, butyl or isobutyl formate, methyl, ethyl, propyl, isopropyl, butyl, isobutyl or secbutyl, amyl, isoamyl, hexyl, cyclohexyl or benzyl acetate, methyl, ethyl or butyl propionate; ketones, especially those having 3 to 10 C atoms in the molecule, such as, for example, acetone, methyl ethyl ketone, methyl n-propyl ketone, diethyl ketone, 2-hexanone, 3-hexanone, di-n-propyl ketone, di-iso-propyl ketone, di-iso-butyl ketone, cyclopentanone, cyclohexanone, methylcyclohexanone, dimethylcyclohexanone, benzophenone, acetophenone; aliphatic hydrocarbons such as, for example, hexane, heptane, low- and high-boiling petroleum ethers, special grades of petroleum spirit, and white spirit; cycloaliphatic hydrocarbons such as, for example, cyclopentane, cyclohexane, methylcyclohexane, tetralin, decalin; aromatic hydrocarbons such as, for example, benzene, toluene, o-, m- and p-xylene, ethylbenzene; halogenated aliphatic or aromatic hydrocarbons such as, for example, methylene chloride, chloroform, carbon tetrachloride, 1,2-dichloroethane, chlorobenzene, dichlorobenzene; hexamethylphosphoric triamide; sulphoxides such as, for example, dimethyl sulphoxide; tetramethylene sulphone; water. It is also possible to use mixtures of various solvents or dispersants, for example water/methanol or, preferably, ethyl acetate/methanol.

The compounds of the formula IA represent compounds of the general formula I according to the invention for the case where $R^1$ is hydrogen.

The acylation of the compound of the formula Ia, which can also be in the form of an acid addition salt, to introduce the radical $R^1 = -COR^4$ can be carried out in a manner known per se using a suitable acylating agent of the formula III

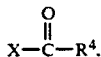
(III)

in which X represents a radical which can be eliminated nucleophilically. Examples of meanings of X in the formula III are, in particular, halogen, preferably —Cl or —Br; —OH; —O—alkyl, in particular having 1 to 5 C atoms; —O— aryl, where the aryl radical is, in particular, a phenyl radical which can also be substituted one or more times by alkyl, in particular methyl, and/or nitro, and is, for example, a tolyl or dinitrophenyl or nitrophenyl radical; —O—CO—$R^4$, —O—CO—O-alkyl, in particular having 1 to 5 C atoms in the alkyl radical, or the radical of an azole or benzazole which has at least 2 N atoms in the quasiaromatic 5-membered ring and is bonded via one N atom.

The acylation is expediently carried out in liquid phase in the presence of an inert solvent, dispersant or diluent or in an excess of the acylating agent, expediently while stirring.

The molar ratio between the compound of the formula Ia and the acylating agent of the formula III in the acylation is theoretically 1:1. It is expedient to use the acylating agent of the formula III in a slight molar excess. Excesses of up to 30 mol-% are adequate as a rule, that is to say the molar ratio between the compound of the formula Ia and the acylating agent of the formula III is normally 1:(1 to 1.3), preferably 1:(1 to 1.2). If an acid is eliminated in the acylation reaction, it is expedient to add an acid trap, such as, for example, an alkali metal hydroxide such as, for example, sodium, potassium or lithium hydroxide, a tertiary organic amine such as, for example, pyridine or triethylamine, an alkali metal carbonate or alkali metal bicarbonate such as, for example, sodium carbonate or sodium bicarbonate, or an alkali metal salt of a weak organic acid such as, for example, sodium acetate. It is also possible to add suitable catalysts in the acylation reaction, such as, for example, 4-dimethylaminopyridine.

The acylation can be carried out in principle at temperatures between $-10°$ C. and the boiling point of the solvent, dispersant or diluent used. In many cases the reaction is carried out at $0°$ to $50°$ C., in particular at $0°$ to $30°$ C. and, preferably, at room temperature.

The compounds of the formula III are acylating agents and thus represent, for example: for X=halogen acid halides or halogenoformic esters, of which acid chlorides and chloroformic esters are preferred; for —OH carboxylic acids; for —O-alkyl and —O-aryl esters, of which the tolyl, 2,4-dinitro- or 4-nitrophenyl esters are preferred; for —O—CO—$R^4$ anhydrides, for —O—CO—O-alkyl mixed carboxylic carbonic anhydrides; or heterocyclic amides or azolides, especially of N,N'-carbonyldiazoles such as, for example, N,N'-carbonyldiimidazole, 2,2'-carbonyldi-1,2,3-triazole, 1,1'-carbonyldi-1,2,4-triazole, N,N'-carbonyldipyrazole, and 2,2'-carbonylditriazole (compare, for example, H. A. Staab, M. Lücking and F. H. Dürr, Chem. Ber. 95, (1962), 1275 et seq., H. A. Staab and A. Mannschreck, Chem. Ber. 95, (1962), 1284 et seq.; H. A. Staab and W. Rohr, "Synthesen mit heterocyclischen Amiden (Azoliden)" (Syntheses with heterocyclic amides (azolides)) in "Neuere Methoden der Präparativen Organischen Chemie" (New Methods of Preparative Organic Chemistry), volume V, Verlag Chemie, 1967, pages 53 et seq., especially pages 65 to 69). The acylating agents of the formula III can be prepared by processes known per se.

When a carboxylic acid is used as acylating agent, it is expedient to add an activating agent which has the task of increasing or activating the acylating power of the carboxylic acid, or of converting the carboxylic acid in situ or, preferably, shortly before the reaction with the compound of the formula Ia into a reactive carboxylic acid derivative of the formula III. Examples of suitable activating agents of this type are: N,N'-disubstituted carbodiimides, especially when they contain at least one secondary or tertiary alkyl radical, such as, for example, diisopropyl, dicyclohexyl- or N-methyl-N'-tert.-butylcarbodiimide (compare Methodicum Chimicum, Verlag G. Thieme, Stuttgart, vol. 6, (1974), page 682/683, and Houben-Weyl, Methoden der Org. Chemie (Methods of Organic Chemistry), vol. 8, (1952), page 521/522); carbonic acid derivatives such as, for example, phosgene, chloroformic esters, especially having 1 to 5 C atoms in the alkyl radical (compare, for example, Tetrahedron Letters 24 (1983), 3365 to 3368); carbonic esters such as, for example, di-N-succinimidyl carbonate, diphthalimidyl carbonate, 1,1'-(carbonyldioxy)-dibenzotriazole or di-2-pyridyl carbonate (compare, for example, Tetrahedron Letters, vol. 25, No. 43, 4943–4946), where appropriate in the presence of suitable catalysts such as, for example, 4-dimethylaminopyridine. Also suitable as activating agents are N,N'-carbonyldiazoles such as, for example, N,N'-carbonyl-diimidazole, 2,2'-carbonyldi-1,2,3-triazole, 1,1'-carbonyldi-1,2,4-triazole, N,N'-carbonyldipyrazole, 2,2'-carbonyl-ditetrazole, N,N'-carbonyldibenzimidazole or N,N'-carbonyldibenzotriazole (compare, for example, H. A. Staab, M. Lücking and F. H. Dürr, loc. cit.; H. A. Staab and A. Mannschreck, loc. cit.; H. A. Staab and W. Rohr loc. cit.). Commercially available N,N'-carbonyldiimidazole is often used as N,N'-carbonyl-diazole. The other N,N'-carbonyl-diazoles can, however, also be obtained easily from the relevant azole and phosgene.

Also suitable as activating agents for carboxylic acids are: derivatives of oxalic acid such as, for example, oxalyl chloride (compare, for example, GB Patent 2,139,225) or N,N'-oxalyl-diazoles such as, for example, 1,1'-oxalyl-di-imidazole, 1,1'-oxalyldi-1,2,4-triazole and 1,1'-oxalyl-di-1,2,3,4-tetrazole (cf. for example, Shizuaka Murata, Bull. Chem. Soc. Jap. 57, 3597–3598 (1984)); methylethylphosphinic anhydride (compare, for example, German Offenlegungsschrift 3,101,427); diphosphorus tetraiodide (Chem. Lett. 1983, 449); dialkyl disulphite (Indian J. Chem. 21, 259 (1982)); or other reactive agents.

Examples of suitable solvents, dispersants or diluents for the acylation are those which have been mentioned for carrying out the cyclization, and in addition, for example, pyridine and amides, such as, for example, dimethylformamide. Besides water, preferred for the acylation are polar organic solvents such as dimethylformamide, dimethyl sulphoxide or pyridine. Also suitable are solvent mixtures such as, for example, a mixture of water and methylene chloride.

If a compound of the formula I with $R^1 = -NO$ is to be prepared, a compound of the formula Ia, which can also be in the form of an acid addition salt, is nitrosated in a manner known per se, expediently in a suitable inert solvent or a solvent mixture, preferably in water, normally at temperatures from 0° to 40° C., and preferably at temperatures from 0° to 10° C. The nitrosation is carried out, for example, with nitrous acid, NO, NOCl or NO-containing gas mixtures. The nitrosation is expediently carried out with nitrous acid, which is advantageously generated from an alkali metal nitrite, for example sodium nitrite, and an acid, especially hydrochloric acid. It is expedient to adjust the aqueous solution of the compound Ia to a pH of 1 to 3 with an acid, especially hydrochloric acid, and to add the alkali metal nitrite in the form of an aqueous solution dropwise to the stirred and cooled solution of the compound.

The compounds of the formula I according to the invention can exist in various configurations in cis or in trans form, it being possible for the trans forms to be racemic mixtures or in optically active form. To prepare these various isomers it is possible to use processes known per se, such as selective synthesis, chiral synthesis or separation of racemic mixtures by known methods.

The substituted 3-aminosydnonimines of the general formula I form acid addition salts with inorganic or organic acids. Suitable to form such acid addition salts are inorganic or organic acids. Examples of suitable acids are hydrogen chloride, hydrogen bromide, phosphoric, nitric, sulphuric, oxalic, lactic, tartaric, acetic, salicyclic, benzoic, formic, propionic, pivalic, diethylacetic, malonic, succinic, pimelic, fumaric, maleic, malic, sulphamic, phenylpropionic, gluconic, ascorbic, isonicotinic, methanesulphonic, p-toluenesulphonic, citric or adipic acid or naphthalendisulphonic acids, in particular naphthalene-1,5-disulphonic acid. Pharmacologically acceptable acid addition salts are preferred. The acid addition salts can be prepared as customary by mixing the components, expediently in suitable solvent or diluent. The acid addition salts are produced in the synthesis of the compounds of the formula Ia.

The required starting compounds of the general formula II can be prepared in a manner known per se by Strecker's amino nitrile synthesis from compounds of the general formula IV

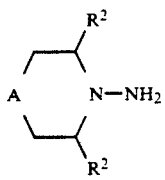
(IV)

in which A and $R^2$ have the abovementioned meanings, by reaction with formaldehyde and hydrocyanic acid or sodium cyanide in a suitable solvent, for example water, the initial result being a compound of the general formula V

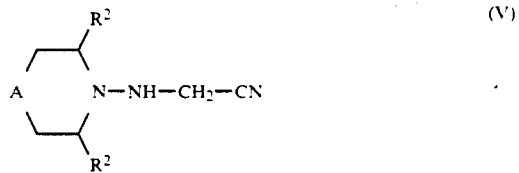
(V)

which is converted by nitrosation into the compound II. The nitrosation is carried out in a known manner, expediently in a suitable inert solvent or solvent mixture, preferably in water, normally at temperatures from 0° to 40° C. and preferably at temperatures from 0° to 10° C. The nitrosation is carried out, for example, with nitrous acid, NO, NOCl or NO-containing gas mixtures. The nitrosation is expediently carried out with nitrous acid, which is advantageously generated from an alkali metal nitrite, for example sodium nitrite, and an acid, especially hydrochloric acid. It is expedient to adjust the aqueous solution of the compound V to a pH of 1 to 3 with an acid, especially hydrochloric acid, and to add the alkali metal nitrite in the form of an aqueous solution dropwise to the stirred and cooled solution of the compound.

The compound II can be isolated from the solution of the compound II obtained in this way, or the solution of the compound II can be subjected directly to the cyclization reaction. However, it is normally appropriate for the subsequent cyclization to take up the nitroso compound II initially in a suitable organic solvent, and to carry out the cyclization to give the compound of the formula Ia in it, where appropriate after addition of another solvent.

Some of the compounds of the general formula IV are known (compare, for example, C. G. Overberger et al., J. Amer. Chem. Soc. 77, (1955) 4100), or they can be prepared, starting from compounds of the general formula VI

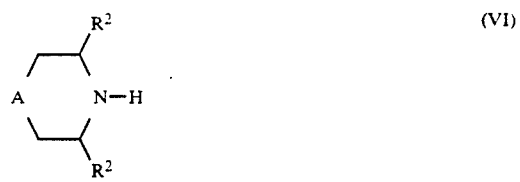
(VI)

either by a) nitrosating a compound of the formula VI to give the N-nitroso compound VII, and then reducing, expediently with lithium aluminium hydride;

(VI) ⟶ 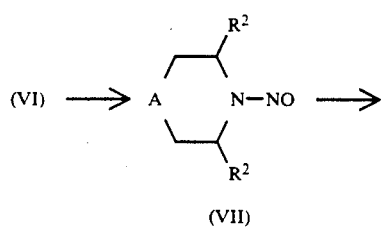 ⟶

(VII)

-continued

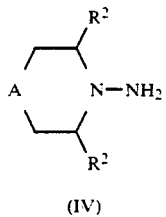

(IV)

or by, in a manner known per se, b) converting a compound of the formula VI with potassium cyanate in acid medium into the urea derivative VIII, which is then converted by oxidation with sodium hypochlorite by Hoffman degradation into the compound IV:

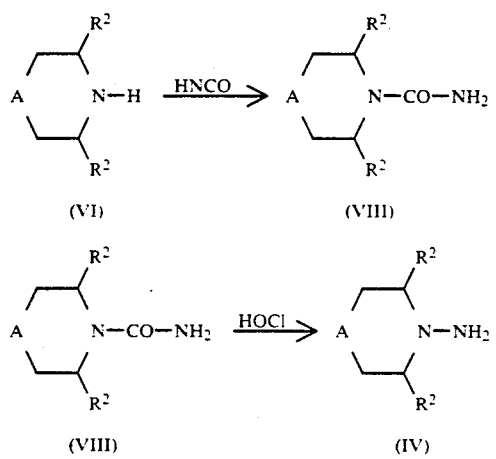

Starting compounds of the formula VI are known (compare, for example, Backer. Van der Ley, Rec. Trav. Chim. Pays-Bas 70, (1951) 564; Berlin, Sytschewa, Z. obsc. Chim. 20, (1950) 640; Idson, Spoerri, J. Amer. Chem. Soc. 76, (1954) 2902) or can be prepared by the processes known for these classes of compounds. Thus, compounds of the formula VI can be prepared, by ring closure with ammonia, for example from compounds of the general formula IX

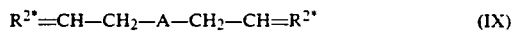

in which A denotes —SO— or —S(O$_2$)— and R$^{2*}$ denotes a radical which is converted on reaction with ammonia, by addition of hydrogen, into the abovementioned radical R$^2$, which compounds can be prepared by methods known per se. The reaction with ammonia can be carried out at temperatures from 20° to 150° C., preferably at 60° to 100° C., with or without solvent.

If the reaction of the compounds of the formula IX is carried out not with ammonia but with hydrazine under the abovementioned conditions, it is possible to obtain compounds of the formula IV directly in the ring closure.

The compounds of the general formula I and the pharmacologically acceptable acid addition salts thereof have valuable pharmacological properties. Their action on the cardiovascular system is particularly pronounced. Compared with known sydnonimine compounds substituted in the 3-position, for example those of EP-B 59,356, as well as the commercially available compound of similar structure, molsidomine, they have, for example, surprisingly a considerably longer duraction of action. For example, they lower the blood pressure as well as the pulmonary artery pressure and the left ventricular end-diastolic pressure and thus contribute to relieving the action of the heart in the sense of an antianginal action, without thereby provoking a reflex tachycardia.

The compounds of the formula I and the pharmacologically acceptable acid addition salts thereof can thus be administered to humans as medicines alone, in mixtures with one another or in the form of pharmaceutical compositions which allow enteral or parenteral use and which contain as active ingredient an effective dose of at least one compound of the formula I, or of an acid addition salt thereof, besides customary pharmaceutically acceptable vehicles and additives.

The medicines can be administered orally, for example in the form of pills, tablets, lacquered tablets, sugar-coated tablets, hard and soft gelatin capsules, solutions, syrups, emulsions or suspensions, or aerosol mixtures. However, administration can also take place rectally, for example in the form of suppositories, or parenterally, for example in the form of injectable solutions, or percutaneously, for example in the form of ointments or tinctures. The pharmaceutical products contain the active compound of formula I or pharmaceutically-acceptable acid-addition salts thereof from about 0.5 to 90 percent by weight.

To prepare the pharmaceutical products it is possible to use pharmaceutically inert inorganic or organic vehicles. Examples which can be used for the preparation of pills, tablets, sugar-coated tablets and hard gelatin capsules are lactose, maize starch or derivatives thereof, talc, stearic acid or salts thereof etc. Examples of vehicles for soft gelatin capsules and suppositories are fats, waxes, semisolid and liquid polyols, natural or hardened oils etc. Examples of suitable vehicles for the preparation of solutions and syrups are water, sucrose, invert sugar, glucose, polyols etc. Examples of suitable vehicles for the preparation of injectable solutions are water, alcohols, glycerol, polyols or vegetable oils.

The pharmaceutical products can, besides the active substances and vehicles, additionally contain additives such as, for example, fillers, extenders, disintegrants, binders, lubricants, wetting agents, stabilizers, emulsifiers, preservatives, sweeteners, colorants, flavourings or aromatizing agents, buffer substances, as well as solvents or solubilizers or agents to achieve a depot effect, and salts to alter the osmotic pressure, coating agents or antioxidants. They can also contain two or more compounds of the formula I or pharmacologically acceptable acid addition salts thereof, and other therapeutically active substances too.

Examples of such other therapeutically active substances are: β-receptor blockers such as, for example, propranolol, pindolol and metoprolol; vasodilators such as, for example, carbocromen; sedatives such as, for example, barbituric acid derivatives, 1,4-benzodiazepines and meprobamate; diuretics such as, for example, chlorothiazide; cardiotonic agents such as, for example, digitalis products; agents to lower blood pressure such as, for example, hydralazine, dihydralazine, prazosin, clonidine, Rauwolfia alkaloids; agents which lower the blood level of fatty acids such as, for example, bezafibrate, fenofibrate; agents for the prophylaxis of thrombosis such as, for example, phenprocoumon, additionally N-substituted N-nitroso-aminoacetonitriles of the formula II, where A and R$^2$ have the meanings mentioned, and where A denotes, in particular, —CH$_2$—, S(O$_2$)—, —O— or a direct bond, and/or R$^2$ denotes methyl. The N-substituted N-nitroso-aminoacetonitriles of the formula II have similarly beneficial pharmacological properties as the compounds of the formula I.

The compounds of the formula I, the pharmacologically acceptable acid addition salts thereof and pharmaceutical products which contain compounds of the formula I or pharmacologically acceptable acid addition salts thereof as active substances can be used in humans to control or prevent diseases of the cardiovascular system, for example as antihypertensive medicines for the various types of high blood pressure, to control or prevent angina pectoris etc. The dosage can vary within wide limits and should be adjusted in each individual case to suit the individual circumstances. In general, an appropriate daily dose on oral administration is about 0.5 to 100 mg, preferably 1 to 20 mg, per individual person. With other modes of administration too, because of the good absorption of the active substances the daily dose is in similar ranges of amounts, that is to say in general likewise 0.5 to 100 mg/person. The daily dose is normally divided into several, for example 2 to 4, partial administrations.

To detect the antianginal action of the compounds according to the invention, investigations were carried out on mongrel days of both sexes under pentobarbital anaesthesia (30 to 40 mg/kg i.v.) or under urethane/chloralose anaesthesia (3 ml/kg urethane/chloralose mixture i.v. = 20 mg/kg chloralose and 250 mg/kg urethane). The animals were ventilated with a bird mark 7 Respirator. The end-expiratory carbon dioxide content (measured with an infrared absorption pen recorder) was between 4.5 and 5% by vol. Throughout the experiment the animals under pentobarbital anaesthesia received a continuous infusion of pentobarbital i.v. = 4 mg (in 6 ml)/kg/h in order to ensure a constant depth of anaesthesia. The animals under urethane/chloralose anaesthesia received no continuous infusion. The infusion was administered through the cephalic vein. After the experimental animals had been prepared about 1 hour was allowed to elapse until all the haemodynamic parameters had reached a steady state. The actual experiment was then started.

To determine the mean peripheral blood pressure (=BP) the peripheral systolic and diastolic blood pressure was measured in the femoral artery using a Statham pressure transducer. A Millar tip catheter advanced via the carotid artery into the left ventricle provided the signal for the left ventricular end-diastolic pressure (=LVEDP) and the heart rate (=HR).

The results obtained are shown in the table below.

| Substance | Dose mg/kg | BP Δmm Hg | LVEDP Δmm Hg | HR Δb/min | DA min |
|---|---|---|---|---|---|
| A | 0.3 | −30 | −3 | +5 | 180 |
| B | 0.3 | −25 | −3 | +5 | 180 |
| C | 0.3 | −35 | −4 | +7 | 200 |
| D | 0.3 | −25 | −4.5 | +4 | 180 |
| E | 0.3 | −35 | −4 | +5 | 150 |
| F | 0.3 | −40 | −7 | +8 | 150 |
| Mol | 0.1 | −18 | −2.3 | +3 | 90 |

The meanings in the above table are as follows:
A = 3-(2,6-Dimethylpiperidin-1-yl)-sydnonimine hydrochloride
B = 3-(2,6-Dimethylpiperidin-1-yl)-N-benzoyl-sydnonimine
C = 3-(2,6-Dimethylpiperidin-1-yl)-N-(allylthio)acetylsydnonimine
D = 3-(2,6-Dimethylpiperidin-1-yl)-N-i-propoxycarbonylsydnonimine
E = 3-(2.6-Dimethylpiperidin-1-yl)-N-butoxy-acetyl sydnonimine
F = 3-(2,6-Dimethylpiperidin-1-yl)-sydnonimine hydrochloride
Mol = Comparison substance molsidomine (3-(morpholin-1-yl)-N-ethoxycarbonyl-sydnonimine)
BP = Mean peripheral blood pressure
LVEDP = Left ventricular end-diastolic pressure
HR = Heart rate (b/min = beats per minute)
DA = Duration of action The preferred compounds of the formula I according to the invention are 3-(2,6-dimethylpiperidin-1-yl)sydnonimine and the pharmacologically acceptable acid addition salts thereof, especially the hydrochloride, as well as 3-(2,6-dimethylpiperidin-1-yl)-N-benzoyl-sydnonimine and 3-(2,6-dimethylpiperidin-1-yl)-N-allylthiomethylcarbonyl-sydnonimine (= 3-(2,6-dimethylpiperidin-1-yl)-N-(allylthio)-acetyl-sydnonimine) and the acid addition salts thereof.

Unless otherwise indicated, the percentages indicated in the examples which follow are percentages by weight. Ratios indicated between components of solvents or eluents are ratios by volume. Where given, m.p. denotes melting point and "decomp." denotes decomposition.

EXAMPLE 1

3-(2,6-dimethylpiperidin-1-yl)-sydnonimine hydrochloride a) A solution of 13.4 g of sodium nitrite in 10 ml of water is added dropwise to a mixture of 29.1 g of N-(2,6-dimethylpiperidin-1-yl)-aminoacetonitrile, 100 ml of water, 100 ml of ethyl acetate and 12 g of concentrated hydrochloric acid and, after stirring at room temperature for 5 hours, the organic phase is separated off, diluted with 20 ml of methanol and stirred in an ice bath. Hydrochloric acid is passed into saturation, and then the mixture is stirred at room temperature for 15 hours and concentrated under water pump vacuum. The residue crystallizes on trituration with diethyl ether. It is filtered off with suction and recrystallized from acetonitrile.

Yield: 18.2 g of 3-(2,6-dimethylpiperidin-1-yl)-sydnonimine hydrochloride

Melting point: 136°-137° C. (decomp.)

b) The starting material 3-(2,6-dimethylpiperidin-1-yl)-aminoacetonitrile required above in a) is prepared as follows:

A solution of 11.5 g of sodium cyanide in 20 ml of water is added to a mixture of 30.0 g of 1-amino-2,6-dimethylpiperidine, 20 g of concentrated hydrochloric acid and 100 ml of water cooled in ice, and the pH is adjusted to 6.5 with hydrochloric acid. Then 19.3 g of a 39% strength aqueous formaldehyde solution are added, and the reaction mixture is stirred at 0° C. for 3 hours and at room temperature for a further 3 hours. The product is extracted with ethyl acetate, and the ethyl acetate phase is washed with dilute acetic acid and dried over sodium sulphate. Remaining after concentration is an oily residue (29.1 g) which is, without further purification, further processed as in a).

EXAMPLE 2

3-(2,6-dimethylpiperidin-1-yl)-N-ethoxycarbonylsydnonimine 3.5 g of sodium bicarbonate are added to a solution of 5 g of 3-(2,6-dimethylpiperidin-1-yl)-sydnonimine hydrochloride, prepared as in Example 1a), in 20 ml of water cooled in ice, and then a solution of 2.5 g of ethyl chloroformate in 20 ml of methylene chloride is added, and the mixture is stirred at room temperature for 4 hours. The organic phase is separated off, dried and concentrated. The residue is triturated with petroleum ether and filtered off with suction.

Yield: 4.2 g
Melting point: 90° to 91° C.

EXAMPLE 3

3-(3,5-Dimethylthiomorpholin-4-yl 1,1-dioxide)-sydnonimine hydrochloride a) A mixture of 32.2 g of diallyl sulphone, 55 g of hydrazine hydrate and 54 ml of water is boiled for 30 minutes. The mixture is stirred in an ice bath, and the precipitate is filtered off with suction and recrystallized from ethanol.

Yield: 16.2 g of 4-amino-3,5-dimethyl-thiomorpholine dioxide
Melting point: 181° to 183° C.

b) A mixture of 16.2 g of 4-amino-3,5-dimethylthiomorpholine dioxide, 9.1 g of concentrated hydrochloric acid, 80 ml of water and 5.6 g of sodium cyanide is cooled to 5° C. and 9.1 g of a 39% strength formaldehyde solution are added (pH=7 to 7.5). The reaction mixture is then stirred at room temperature for 4 hours. While cooling in ice the mixture is acidified (pH=1), and a solution of 6.3 g of sodium nitrite in 25 ml of water is added dropwise. The mixture is then stirred at room temperature for 3 hours, and the solid is filtered off with suction.

Yield: 16.0 g of N-(3,5-dimethylthiomorpholin-4-yl 1,1-dioxide)-N-nitroso-aminoacetonitrile
Melting point: 163° to 165° C.

c) 15.8 g of N-(3,5-dimethylthiomorpholin-4-yl 1,1-dioxide)-N-nitroso-aminoacetonitrile are dissolved in 100 ml of methanol and 100 ml of ethyl acetate and saturated with HCl. The precipitated solid is filtered off with suction, and the filtrate is concentrated. The residue is triturated with absolute ethanol and with ethyl acetate, filtered off with suction and dried.

Yield: 8.5 g of 3-(3,5-dimethylthiomorpholin-4-yl 1,1-dioxide)-sydnonimine hydrochloride
Melting point: 192° C. (decomp.)

EXAMPLE 4

N-Ethoxycarbonyl-3-(3,5-dimethylthiomorpholin-4-yl) 1,1-dioxide)-sydnonimine 3.9 g of sodium bicarbonate are added to a solution of 5.8 g of 3-(3,5-dimethylthomorpholin-4-yl 1,1-dioxide)-sydnonimine hydrochloride in 20 ml of water cooled in ice, and then a solution of 3 g of ethyl chloroformate in 20 ml of methylene chloride is added, and the mixture is stirred in the ice bath for 6 hours. The organic phase is separated off, dried and concentrated. The residue is worked up by column chromatography (silica gel, CH$_2$Cl$_2$:MeOH=97:3). The appropriate fractions are concentrated and the residue is triturated with diethyl ether and filtered off with suction.

Yield: 2.1 g
Melting point: 180° C. (decomp.)

EXAMPLE 5

N-Benzoyl-3-(2,6-dimethylpiperidin-1-yl)-sydnonimine is prepared in analogy to Example 2 by reaction with 3.2 g of benzoyl chloride in place of 2.5 g of ethyl chloroformate, and is recrystallized from isopropanol/petroleum ether.

Yield: 3.4 g
Melting point: 141°-142° C.

EXAMPLE 6

N-Cyclohexylcarbonyl-3-(2,6-dimethylpiperidin-1-yl)-sydnonimine hydrochloride is prepared in analogy to Example 2 by use of 3.3 g of cyclohexanecarbonyl chloride in place of 2.5 g of ethyl chloroformate. The oily base is dissolved in ethyl acetate and precipitated as the salt with hydrogen chloride.

Yield: 3.8 g
Melting point: 111° C. (decomp.)

EXAMPLE 7

N-(Allylthio)-acetyl-3-(2,6-dimethylpiperidin-1-yl)-sydnonimine hydrochloride is prepared in analogy to Example 2 by use of 3.4 g of (allylthio)-acetyl chloride in place of 3.3 g of cyclohexanecarbonyl chloride, and is precipitated from diisopropyl ether with hydrogen chloride.

Yield: 2.9 g
Melting point: 91° C. (decomp.)

EXAMPLE 8

N-n-Butoxy-acetyl-3-(2,6-dimethylpiperidin-1-yl)-sydnonimine hydrochloride is prepared in analogy to Example 2 by use of 3.4 g of n-butoxy-acetyl chloride in place of allylthioacetyl chloride, and is precipitated from diethyl ether with HCl.

Yield: 2.3 g
Melting point: 101° C. (decomp.)

EXAMPLE 9

N-Isopropoxycarbonyl-3-(2,6-dimethylpiperidin-1-yl)-sydnonimine is prepared in analogy to Example 2 (2.7 g of isopropyl chloroformate in place of 2.5 g of ethyl chloroformate) and recrystallized from isopropyl ether.

Yield: 4.0 g
Melting point: 89°-90° C.

EXAMPLE 10

N-(2-Isopropoxy-ethoxy-carbonyl)-3-(2,6-dimethylpiperidin-1-yl)-sydnonimine is prepared in analogy to Example 2 (3.0 g of isopropoxyethyl chloroformate in place of 2.5 g of ethyl chloroformate).

Yield: 4.5 g
Melting point: oil

EXAMPLE 11

N-(Imidazol-1-yl)-carbonyl)-3-(2,6-dimethylpiperidin-1-yl-sydnonimine.

A mixture of 3.7 g of 3-(2,6-dimethylpiperidin-1-yl)-sydnonimine hydrochloride, 2.4 g of carbonyl diimidazole, 2.5 g of sodium bicarbonate and 50 ml of methylene chloride is stirred at room temperature for 16 hours. After removal of the solvent in vacuo, the residue is taken up in 40 ml of 2N hydrochloric acid and extracted by shaking with diethyl ether. The aqueous phase is neutralized and then the product is extracted with diethyl ether, and the ether phase is dried and concentrated. The residue is recrystallized from isopropyl ether.

Yield: 2.8 g
Melting point: 119°–120° C.

EXAMPLE 12

3-(2,5-Dimethylpyrrolidin-1-yl)-sydnonimine hydrochloride

This compound is prepared in analogy to Example 1 starting from 11.4 g of N-(2,5-dimethylpyrrolidin-1-yl)-aminoacetonitrile and 7.6 g of sodium nitrite.

Yield: 4.4 g
Melting point: 120° C. (decomp.)

EXAMPLE 13

N-Nitroso-3-(2,6-dimethylpiperidino)-sydnonimine

This compound is obtained by reaction of 3 g of 3-(2,6-dimethylpiperidino)-sydnonimine hydrochloride with 0.93 g of sodium nitrite in water, with addition of sufficient hydrochloric acid for the pH to be between 2 and 3.

Yield: 2.1 g
Melting point: 74° C. (decomp.)

The compounds of the formula Ib indicated in the table which follows are prepared in analogy to Example 2.

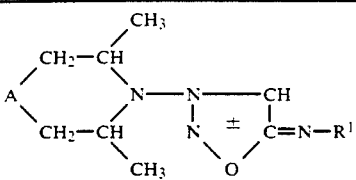
(Ib)

| Nr. | A | R¹ | m.p. °C. |
|---|---|---|---|
| 14 | —CH₂— | —COCH₃ | 115 (decomp.) |
| 15 | —CH₂— | —COCH(CH₃)₂ | 131 (decomp.) |
| 16 | —CH₂— | —CO—C₆H₄—Cl (4-Cl) | 128 |
| 17 | —CH₂— | —CO—C₆H₄—O—COCH₃ (2-OCOCH₃) | 91 (decomp.) |
| 18 | — | —CO—C₆H₄—F (4-F) | 132 |
| 19 | — | —CO—C₆H₄—CH₃ (3-CH₃) | 109 |
| 20 | — | —CO—C₆H₃(OCH₃)₂ (3,4-di-OCH₃) | 138 |
| 21 | —CH₂— | —CO—C₆H₄—OCH₃ (4-OCH₃) | 129–131 |
| 22 | —CH₂— | —CO—C₆H₄—Br (4-Br) | 138 (decomp.) |
| 23 | —CH₂— | —CO—C₆H₄—C(CH₃)₃ (4-tBu) | 118 (decomp.) (hydrochloride) |
| 24 | —CH₂— | —CO—C₆H₄—Cl (3-Cl) | 131–133 |
| 25 | —CH₂— | —CO—C₆H₄—Cl (2-Cl) | 101–102 |
| 26 | —CH₂— | —CO—C₆H₃Cl₂ (3,4-di-Cl) | 88–90 |
| 27 | —CH₂— | —CO—C₆H₂(OCH₃)₃ (3,4,5-tri-OCH₃) | 149–151 |
| 28 | —CH₂— | —CO—(3-pyridyl) | 97–98 |
| 29 | —CH₂— | —CO—(2-thienyl) | 117–118 |

-continued $$\begin{matrix} & CH_3 \\ CH_2-CH & \\ A & N-N-CH \\ CH_2-CH & N \pm C=N-R^1 \\ & CH_3 & O \end{matrix}$$ (Ib)

| Nr. | A | R¹ | m.p. °C. |
|---|---|---|---|
| 30 | —CH₂— | —CO—C₆H₄—(pyrazolyl) | 108–110 |
| 31 | —CH₂— | —CO—C₆H₄—CF₃ | 120–121 |
| 32 | —CH₂— | —CO—C₆H₄(SCH₃) | 86–88 |
| 33 | —CH₂— | —CO—CH=CH—C₆H₅ | 149–152 |
| 34 | —CH₂— | —CO—C₆H₄—O(CH₂)₃—CH₃ | 97–99 (decomp.) (hydrochloride) |
| 35 | —CH₂— | —CO₂(CH₂)₉—CH₃ | 104 (decomp.) (hydrochloride) |
| 36 | —CH₂— | —CO₂(CH₂)₁₇—CH₃ | 81 (decomp.) (hydrochloride) |

Where "-" is put for A in Examples 18 to 20 in the table, this means a direct bond, that is to say a 2,5-dimethylpyrrolidin-1-yl radical is present in the 3 position of the sydnonimine in Examples 18 to 20.

Pharmaceutical products are described in Examples A to F which follow.

EXAMPLE A

Soft Gelatin Capsules Containing 5 mg of Active Substance Per Capsule

| | per capsule |
|---|---|
| Active substance | 5 mg |
| Triglyceride mixture fractionated from coconut oil | 150 mg |
| Capsule content | 155 mg |

EXAMPLE B

Injectable Solution Containing 1 mg of Active Substance Per ml

| | per ml |
|---|---|
| Active substance | 1.0 mg |
| Polyethylene glycol 400 | 0.3 ml |
| Sodium chloride | 2.7 mg |
| Water for injections | ad 1 ml |

EXAMPLE C

Emulsion Containing 3 mg of Active Substance Per 5 ml

| | per 100 ml of emulsion |
|---|---|
| Active substance | 0.06 g |
| Neutral oil | q.s. |
| Sodium carboxymethylcellulose | 0.6 g |
| Polyoxyethylene stearate | q.s. |
| Glycerol, pure | 0.2 to 2.0 g |
| Flavouring | q.s. |
| Water (deionized or distilled) | ad 100 ml |

EXAMPLE D

Rectal Drug Form Containing 4 mg of Active Substance Per Suppository

| | per suppository |
|---|---|
| Active substance | 4 mg |
| Suppository base | ad 2 g |

EXAMPLE E

Tablets Containing 2 mg of Active Substance Per Tablet

| | per tablet |
|---|---|
| Active substance | 2 mg |
| Maize starch | 150 mg |
| Lactose | 60 mg |
| Microcrystalline cellulose | 50 mg |
| Polyvinylpyrrolidone | 20 mg |
| Magnesium stearate | 2 mg |
| Sodium carboxymethyl starch | 25 mg |
| | 309 mg |

EXAMPLE F

Sugar-Coated Tablets Containing 1 mg of Active Substance Per Tablet

| | per tablet |
|---|---|
| Active substance | 1 mg |
| Maize starch | 100 mg |
| Lactose | 60 mg |
| sec. Calcium phosphate | 30 mg |
| Soluble starch | 3 mg |
| Magnesium stearate | 2 mg |
| Colloidal silica | 4 mg |
| | 200 mg |

It is to be understood that the above described embodiments of the invention are illustrative only, and that

We claim:
1. Substituted 3-Aminisydonimines of the formula I

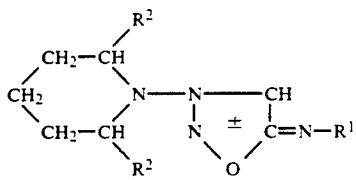

and the pharmaceutically acceptable acid addition salts thereof, in which
$R^1$ is selected from the group consisting of hydrogen and $-COR^4$,
$R^2$ is selected from the group consisting of alkyl having 1 to 4 C atoms and phenylalkyl having 1 to 4 C atoms in the alkyl radical,
$R^4$ is selected from the group consisting of an aliphatic radical which has 1 to 6 C atoms and can also be substituted by alkoxy having 1 to 6 C atoms or by an aliphatic thio radical having up to 4 C atoms; a cycloaliphatic radical having 5 to 7 C atoms; an alkoxy radical which has 1 to 18 C atoms and can also be substituted by alkoxy having 1 to 6 C atoms; an aryl radical having 6 or 10 C atoms; an aryl radical which has 6 or 10 atoms and is mono-, di- or trisubstituted by 1 to 3 halogen atoms and/or 1 to 3 alkyl radicals having 1 to 4 C atoms and/or 1 to 3 alkyl radicals having 1 to 4 C atoms and/or 1 or 3 alkoxy radicals having 1 to 4 C atoms and/or 1 or 2 alkyl- carbonyloxy radicals having 1 to 4 C atoms, and/or 1 to 3 alkylthio radicals having 1 to 4 C atoms and/or a tri-fluoromethyl radical and/or an imidazole radical; an imidazolyl radical; a pyridyl radical; a thienyl radical or a styryl radical.

2. Substituted 3-aminosydnonimines according to claim 1 characterized in that $R^2$ methyl.

3. A pharmaceutical product useful for controlling and/or preventing cardiovascular diseases and having, as active component, from about 0.5 to 90 percent by weight of a compound of claim 1 or of a pharmaceutically-acceptable acid-addition salt thereof together with a pharmaceutically-acceptable vehicle and, optionally, a pharmaceutically-acceptable additive.

4. A process for controlling or preventing cardiovascular diseases which comprises administering an effective amount of a pharmaceutically-active substituted 3-aminosydnonimine of claim 1, or of a pharmaceutically-acceptable acid-addition salt thereof, to a host in need thereof.

5. Substituted 3-aminosydnonimines according to claim 1 characterized in that the radicals $R^2$ are in cis-position relative to one another.

6. 3-(2,6-Dimethylpiperidin-1-yl)-sydnonimine and the pharmacologically acceptable acid addition salts thereof.

7. A pharmaceutical product useful for treating angina pectoris and/or high blood pressure and having, as active component, from about 0.5 to 90 percent by weight of the compound of claim 6 or of a pharmaceutically-acceptable acid-addition salt thereof together with a pharmaceutically-acceptable vehicle and, optionally, a pharmaceutically-acceptable additive.

8. A process for treating angina pectoris and/or high blood pressure which comprises administering an effective amount of the 3-aminosydnonimine of claim 6 or of a pharmaceutically-acceptable acid-addition salt thereof, to a host in need thereof.

9. 3-(2,6-Dimethylpiperidin-1-yl)-N-(p-anisoyl) sydnonimine and the pharmacologically acceptable acid addition salts thereof.

10. A pharmaceutical product useful for treating angina pectoris and/or high blood pressure and having, as active component, from about 0.5 to 90 percent weight of the compound of claim 9 or of a pharmaceutically-acceptable acid addition salt thereof together with a pharmaceutically-acceptable vehicle and, optionally, a pharmaceutically-acceptable additive.

11. A process for treating angina pectoris and/or high blood pressure which comprises administering an effective amount of the 3-aminosydnonimine of claim 9, or of a pharmaceutically-acceptable acid-addition salt thereof, to a host in need thereof.

* * * * *